US007618789B2

(12) United States Patent
Roberts et al.

(10) Patent No.: US 7,618,789 B2
(45) Date of Patent: Nov. 17, 2009

(54) USE OF SEMENOGELIN IN THE DIAGNOSIS, PROGNOSIS AND TREATMENT OF CANCER

(75) Inventors: David D. Roberts, Bethesda, MD (US); Henry C. Krutzsch, Bethesda, MD (US); Christine Krutzsch, legal representative, Bethesda, MD (US)

(73) Assignee: The United States of America as represented by the Secretary of Department of Health and Human Services, Washington, DC (US)

( * ) Notice: Subject to any disclaimer, the term of this patent is extended or adjusted under 35 U.S.C. 154(b) by 578 days.

(21) Appl. No.: 10/474,213

(22) PCT Filed: Apr. 3, 2002

(86) PCT No.: PCT/US02/10535

§ 371 (c)(1),
(2), (4) Date: Apr. 20, 2004

(87) PCT Pub. No.: WO02/081630

PCT Pub. Date: Oct. 17, 2002

(65) Prior Publication Data

US 2004/0214248 A1 Oct. 28, 2004

Related U.S. Application Data

(60) Provisional application No. 60/281,994, filed on Apr. 6, 2001.

(51) Int. Cl.
*G01N 33/574* (2006.01)
(52) U.S. Cl. .................................... 435/7.23
(58) Field of Classification Search .............. 435/7.23
See application file for complete search history.

(56) References Cited

U.S. PATENT DOCUMENTS

| | | | |
|---|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,569,788 A | 2/1986 | Mulshine et al. |
| 5,279,721 A | 1/1994 | Schmid |
| 5,599,686 A | 2/1997 | DeFeo-Jones et al. |
| 5,866,679 A | 2/1999 | DeFeo-Jones et al. |
| 5,972,615 A | 10/1999 | An et al. |
| 6,040,138 A | 3/2000 | Lockhart et al. |
| 6,130,204 A | 10/2000 | DeFeo-Jones et al. |
| 6,143,864 A | 11/2000 | DeFeo-Jones et al. |
| 6,171,796 B1 | 1/2001 | An et al. |
| 6,177,404 B1 | 1/2001 | DeFeo-Jones et al. |
| 6,197,506 B1 | 3/2001 | Fodor et al. |
| 6,265,540 B1 | 7/2001 | Isaacs et al. |
| 6,335,170 B1 | 1/2002 | Orntoft |
| 2001/0007748 A1 | 7/2001 | An et al. |

FOREIGN PATENT DOCUMENTS

| | | |
|---|---|---|
| WO | WO 98/52966 A1 | 11/1998 |
| WO | WO 99/04265 A2 | 1/1999 |
| WO | WO 99/61471 A2 | 12/1999 |
| WO | WO 01/93861 A1 | 12/2001 |

OTHER PUBLICATIONS

Drexler et al (Leukemia and Lymphoma, 1993, 9:1-25).*
Embleton et al (Immunol Ser, 1984, 23:181-207).*
Hsu (in Tissue Culture Methods and Applications, Kruse and Patterson, Eds, 1973, Academic Press, NY, see abstract, p. 764).*
Weiner (Seminars Oncology, vol. 26, No. 4, 1999, pp. 41-50).*
Kaiser (Science, 2006, 3.13:1370).*
Internal Medicine, 4th Edition, Editor-in-chief Jay Stein, Elsevier Science, 1998 Chapters 71-72, pp. 699-715.*
Lilja et al (PNAS, 1992, 89:4559-4563.*
Rodrigues et al. (Clinical Cancer Research 2001; vol. 7: 854-860).*
Lundwall et al .(Molecular Human Reproduction 2002: vol. 8: 805-811).*
Freshney (Culture of Animal Cells, A Manual of Basic Technique, Alan R. Liss, Inc., 1983, New York, p. 4).*
Dermer (Bio/Technology, 1994, 12:320).*
Bjartell et al., "Distribution and Tissue Expression of Semenogelin I and II in Man as Demonstrated by In Situ Hybridization and Immunocytochemistry," *J. Androl.*, 17(1), 17-26 (1996).
Krutzsch et al., "Identification of an $\alpha_3\beta_1$ Integrin Recognition Sequence in Thrombospondin-1," *J. Biol. Chem.*, 274(34), 24080-24086 (1999).
Malm et al., "Isolation and Characterization of the Major Gel Proteins in Human Semen, Semenogelin I and Semenogelin II," *Eur. J. Biochem.*, 238, 48-53 (1996).
Rodrigues et al., "Semenogelins Are Ectopically Expressed in Small Cell Lung Carcinoma," *Clin. Can. Res.*, 7, 854-860 (2001).

(Continued)

*Primary Examiner*—Brandon J Fetterolf
(74) *Attorney, Agent, or Firm*—Leydig, Voit & Mayer, Ltd.

(57) ABSTRACT

Method of diagnosing cancer in a male mammal comprising obtaining and assaying a test sample for an increased level of semenogelin; method of diagnosing cancer in a female mammal comprising obtaining and assaying a test sample for the presence of semenogelin; methods of prognosticating and assessing the effectiveness of treatment of a cancer in a mammal comprising measuring the level of semenogelin in a test sample; method of inducing an immune response to a cancer in a mammal comprising administering to the mammal a composition comprising (a) an immune-response inducing effective amount of (i) semenogelin or (ii) antibody thereto or (b) a recombinant vector encoding and expressing an immune-response inducing effective amount of (i) or (ii); and composition comprising a carrier and (a) an immune-response inducing effective amount of (i) a polypeptide of any of SEQ ID NOS:1-27 or (ii) antibody thereto or (b) a recombinant vector encoding and expressing an immune-response inducing effective amount of (i) or (ii).

16 Claims, No Drawings

OTHER PUBLICATIONS

Walker et al., "Isothermal in vitro Amplification of DNA by a Restriction Enzyme/DNA Polymerase System," *Proc. Natl. Acad. Sci. USA*, 89, 392-396 (1992).

Lundwall et al., "Semenogelin I and II, the predominant human seminal plasma proteins, are also expressed in non-genital tissues," *Mol. Hum. Reprod.*, 8 (9), 805-810 (2002).

* cited by examiner

SEQUENCE LISTING

```
<160> NUMBER OF SEQ ID NOS: 28

<210> SEQ ID NO 1
<211> LENGTH: 13
<212> TYPE: PRT
<213> ORGANISM: Homo sapiens

<400> SEQUENCE: 1

Gln His Leu Gly Gly Ser Gln Gln Leu Leu Asn Tyr Lys
1               5                   10

<210> SEQ ID NO 2
<211> LENGTH: 12
<212> TYPE: PRT
<213> ORGANISM: Homo sapiens

<400> SEQUENCE: 2

His Leu Gly Gly Ser Gln Gln Leu Leu His Asn Lys
1               5                   10

<210> SEQ ID NO 3
<211> LENGTH: 10
<212> TYPE: PRT
<213> ORGANISM: Homo sapiens

<400> SEQUENCE: 3

Gly His Tyr Gln Asn Val Val Asp Val Arg
1               5                   10

<210> SEQ ID NO 4
<211> LENGTH: 10
<212> TYPE: PRT
<213> ORGANISM: Homo sapiens

<400> SEQUENCE: 4

Gly His Tyr Gln Asn Val Val Glu Val Arg
1               5                   10

<210> SEQ ID NO 5
<211> LENGTH: 9
<212> TYPE: PRT
<213> ORGANISM: Homo sapiens

<400> SEQUENCE: 5

Gln Asp Leu Leu Ser His Glu Gln Lys
1               5

<210> SEQ ID NO 6
<211> LENGTH: 10
<212> TYPE: PRT
<213> ORGANISM: Homo sapiens
```

-continued

```
<400> SEQUENCE: 6

Glu Gln Asp Leu Leu Ser His Glu Gln Lys
1               5                   10

<210> SEQ ID NO 7
<211> LENGTH: 11
<212> TYPE: PRT
<213> ORGANISM: Homo sapiens

<400> SEQUENCE: 7

Ile Ser Tyr Gln Ser Ser Ser Thr Glu Glu Arg
1               5                   10

<210> SEQ ID NO 8
<211> LENGTH: 11
<212> TYPE: PRT
<213> ORGANISM: Homo sapiens

<400> SEQUENCE: 8

Ile Pro Ser Gln Ala Gln Glu Tyr Gly His Lys
1               5                   10

<210> SEQ ID NO 9
<211> LENGTH: 8
<212> TYPE: PRT
<213> ORGANISM: Homo sapiens

<400> SEQUENCE: 9

Gly Gln His Tyr Phe Gly Gln Lys
1               5

<210> SEQ ID NO 10
<211> LENGTH: 17
<212> TYPE: PRT
<213> ORGANISM: Homo sapiens

<400> SEQUENCE: 10

Ser Gln Asn Gln Val Thr Ile Pro Ser Gln Asp Gln Glu His Gly His
1               5                   10                  15

Lys

<210> SEQ ID NO 11
<211> LENGTH: 12
<212> TYPE: PRT
<213> ORGANISM: Homo sapiens

<400> SEQUENCE: 11

Lys Ser Gln Gln Tyr Asp Leu Asn Ala Leu His Lys
1               5                   10

<210> SEQ ID NO 12
<211> LENGTH: 19
<212> TYPE: PRT
<213> ORGANISM: Homo sapiens

<400> SEQUENCE: 12

Ser Gln Ile Gln Thr Pro Asn Pro Asn Gln Asp Gln Trp Ser Gly Gln
1               5                   10                  15

Asn Ala Lys
```

```
<210> SEQ ID NO 13
<211> LENGTH: 14
<212> TYPE: PRT
<213> ORGANISM: Homo sapiens

<400> SEQUENCE: 13

Gly Ser Ile Ser Ile Gln Thr Glu Glu Lys Ile His Gly Lys
1               5                   10

<210> SEQ ID NO 14
<211> LENGTH: 11
<212> TYPE: PRT
<213> ORGANISM: Homo sapiens

<400> SEQUENCE: 14

Ser Gln Gln Tyr Asp Leu Asn Ala Leu His Lys
1               5                   10

<210> SEQ ID NO 15
<211> LENGTH: 11
<212> TYPE: PRT
<213> ORGANISM: Homo sapiens

<400> SEQUENCE: 15

Gly His Phe His Met Ile Val Ile His His Lys
1               5                   10

<210> SEQ ID NO 16
<211> LENGTH: 8
<212> TYPE: PRT
<213> ORGANISM: Homo sapiens

<400> SEQUENCE: 16

Leu Trp Val His Gly Leu Ser Lys
1               5

<210> SEQ ID NO 17
<211> LENGTH: 13
<212> TYPE: PRT
<213> ORGANISM: Homo sapiens

<400> SEQUENCE: 17

Asp Val Ser Gln Ser Ser Ile Ser Phe Gln Ile Glu Lys
1               5                   10

<210> SEQ ID NO 18
<211> LENGTH: 20
<212> TYPE: PRT
<213> ORGANISM: Homo sapiens

<400> SEQUENCE: 18

Gly Ser Phe Ser Ile Gln His Thr Tyr His Val Asp Ile Asn Asp His
1               5                   10                  15

Asp Trp Thr Arg
            20

<210> SEQ ID NO 19
<211> LENGTH: 20
<212> TYPE: PRT
<213> ORGANISM: Homo sapiens
```

```
<400> SEQUENCE: 19

Thr Gln Gly Gly Ser Gln Ser Ser Tyr Val Leu Gln Thr Glu Glu Leu
1               5                   10                  15

Val Val Asn Lys
            20

<210> SEQ ID NO 20
<211> LENGTH: 10
<212> TYPE: PRT
<213> ORGANISM: Homo sapiens

<400> SEQUENCE: 20

His Leu Ala Gln His Leu Asn Asn Asp Arg
1               5                   10

<210> SEQ ID NO 21
<211> LENGTH: 12
<212> TYPE: PRT
<213> ORGANISM: Homo sapiens

<400> SEQUENCE: 21

Gly Ile Ser Ser Gln Tyr Ser Asn Thr Glu Glu Arg
1               5                   10

<210> SEQ ID NO 22
<211> LENGTH: 10
<212> TYPE: PRT
<213> ORGANISM: Homo sapiens

<400> SEQUENCE: 22

Leu His Tyr Gly Glu Asn Gly Val Gln Lys
1               5                   10

<210> SEQ ID NO 23
<211> LENGTH: 14
<212> TYPE: PRT
<213> ORGANISM: Homo sapiens

<400> SEQUENCE: 23

Asp Val Ser Gln Ser Ser Ile Tyr Ser Gln Thr Glu Glu Lys
1               5                   10

<210> SEQ ID NO 24
<211> LENGTH: 14
<212> TYPE: PRT
<213> ORGANISM: Homo sapiens

<400> SEQUENCE: 24

Gln Ile Thr Ile Pro Ser Gln Glu Gln Glu His Ser Gln Lys
1               5                   10

<210> SEQ ID NO 25
<211> LENGTH: 13
<212> TYPE: PRT
<213> ORGANISM: Homo sapiens

<400> SEQUENCE: 25

Leu Pro Ser Glu Phe Ser Gln Phe Pro His Gly Gln Lys
1               5                   10

<210> SEQ ID NO 26
<211> LENGTH: 22
<212> TYPE: PRT
<213> ORGANISM: Homo sapiens
```

-continued

```
<400> SEQUENCE: 26

His Gln His Gly Ser His Gly Gly Leu Asp Ile Val Ile Ile Glu Gln
1               5                   10                  15

Glu Asp Asp Ser Asp Arg
            20

<210> SEQ ID NO 27
<211> LENGTH: 14
<212> TYPE: PRT
<213> ORGANISM: Homo sapiens

<400> SEQUENCE: 27

Asp Ile Phe Ser Thr Gln Asp Glu Leu Leu Val Tyr Asn Lys
1               5                   10

<210> SEQ ID NO 28
<211> LENGTH: 12
<212> TYPE: PRT
<213> ORGANISM: Artificial
<220> FEATURE:
<223> OTHER INFORMATION: Synthetic peptide

<400> SEQUENCE: 28

Phe Gln Gly Val Leu Gln Asn Val Arg Phe Val Phe
1               5                   10
```

USE OF SEMENOGELIN IN THE DIAGNOSIS, PROGNOSIS AND TREATMENT OF CANCER

This application is the U.S. national phase of PCT/US02/10535, which was filed on Apr. 3, 2002, and which claims the benefit of U.S. provisional patent application no. 60/281,994, which was filed on Apr. 6, 2001.

FIELD OF THE INVENTION

This invention pertains to the use of semenogelin in the diagnosis, prognosis and treatment of cancer, particularly small-cell lung cancer.

BACKGROUND OF THE INVENTION

The American Cancer Society estimates the lifetime risk that an individual will develop cancer is 1 in 2 for men and 1 in 3 for women. The development of cancer, while still not completely understood, can be enhanced as a result of a variety of risk factors. For example, exposure to environmental factors (e.g., tobacco smoke) might trigger modifications in certain genes, thereby initiating cancer development. Alternatively, these genetic modifications may not require an exposure to environmental factors to become abnormal. Indeed, certain mutations (e.g., deletions, substitutions, etc.) can be inherited from generation to generation, thereby imparting an individual with a genetic predisposition to develop cancer.

Currently, the survival rates for many cancers are on the rise. One reason for this success is improvement in the detection of cancer at a stage at which treatment can be effective. Indeed, it has been noted that one of the most effective means to survive cancer is to detect its presence as early as possible. According to the American Cancer Society, the relative survival rate for many cancers would increase by about 15% if individuals participated in regular cancer screenings. Therefore, it is becoming increasingly useful to develop novel diagnostic tools to detect the cancer either before it develops or at an as early stage of development as possible.

One popular way of detecting cancer early is to analyze the genetic makeup of an individual to detect the presence or expression levels of a marker gene(s) related to the cancer. For example, there are various diagnostic methods that analyze a certain gene or a pattern of genes to detect cancers of the breast, tongue, mouth, colon, rectum, cervix, prostate, testis, and skin. Recently, measuring the level of expression of semenogelin has been found to be useful in the detection of prostate cancer.

Semenogelin is known to be the predominant protein in human semen. Normally, it is synthesized by the secretory epithelium of the seminal vesicles as a 461 amino acid precursor protein. Following cleavage of a predominantly hydrophobic signal peptide, the secreted protein contains 439 amino acid residues. Semenogelins I and II (hereinafter referred to as "SgI" and "SgII," respectively) are two separate gene products resulting from the expression of semenogelin and are normally responsible for the gel formation in semen. SgI is a single-chain, non-glycosylated protein of 439 amino acids, whereas SgII contains 559 amino acids (Lilja et al., *Proc. Natl. Acad. Sci. USA.* 89 (10): 4559-4563 1992). Degradation of SgI and SgII is due to the proteolytic action of prostate-specific antigen (PSA), which also has been shown to be helpful in diagnosing prostate cancer.

While semenogelin has been detected in human semen, histological analyses have failed to detect semenogelin expression in any normal human tissue other than seminal vesicle epithelium and epidymis (Herr et al., Biol Reprod. 40: 333-342 (1989); Evans et al., *Anat Rec.* 214: 372-377 (1986); and Bjartell et al., *J Androl.* 17: 17-26 (1996). It has also been shown that a decrease in expression of semenogelin mRNA, as detected by RT-PCR, is indicative of prostate cancer (see, e.g., U.S. Pat. No. 5,972,615).

A need remains for additional ways to diagnose, prognosticate, and treat cancer. The invention provides such methods. These and other advantages of the invention, as well as additional inventive features, will be apparent from the description of the invention provided herein.

BRIEF SUMMARY OF THE INVENTION

The invention provides a method of diagnosing cancer in a male mammal, wherein the cancer is other than prostate cancer, which method comprises obtaining a test sample from the male mammal and subsequently assaying the test sample for an increased level of semenogelin, wherein the increased level of semenogelin in the test sample is diagnostic for the cancer. The invention also provides a method of diagnosing cancer in a female mammal, which method comprises obtaining a test sample from the female mammal and subsequently assaying the test sample for the presence of semenogelin, wherein the presence of semenogelin in the test sample is diagnostic for the cancer. Also provided by the invention is a method of prognosticating a cancer in a mammal, wherein the cancer is other than prostate cancer and semenogelin is a marker for the cancer, which method comprises measuring the level of semenogelin in a test sample obtained from the mammal, wherein the level of semenogelin in the test sample is indicative of the prognosis of the cancer in the mammal. Further provided is a method of assessing the effectiveness of treatment of a cancer in a mammal, wherein the cancer is other than prostate cancer and semenogelin is a marker for the cancer, which method comprises measuring the level of semenogelin in a test sample obtained from the mammal, wherein the level of semenogelin in the test sample is indicative of the effectiveness of the treatment of the cancer in the mammal. Still further provided is a method of inducing an immune response to a cancer in a mammal, wherein the cancer is other than prostate cancer and semenogelin is a marker for the cancer, which method comprises administering to the mammal a composition comprising (a) an immune-response inducing effective amount of (i) a semenogelin protein or polypeptide fragment thereof or (ii) an antibody or antigenically reactive fragment thereof that is specific for a semenogelin protein or polypeptide fragment thereof or (b) a recombinant vector encoding and expressing an immune-response inducing effective amount of (i) or (ii), whereupon an immune response to the cancer is induced. The invention further provides a composition comprising a pharmaceutically acceptable carrier and (a) an immune-response inducing effective amount of (i) a polypeptide of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 or (ii) an antibody or antigenically reactive fragment thereof that is specific for a polypeptide of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 or (b) a recombinant vector encoding and expressing an immune-response inducing effective amount of (i) or (ii).

DETAILED DESCRIPTION OF THE INVENTION

The invention provides a method of diagnosing cancer in a male mammal, wherein the cancer is other than prostate cancer. The method comprises: (a) obtaining a test sample from the male mammal, and (b) assaying the test sample for an increased level of semenogelin, wherein the increased level of semenogelin in the test sample is diagnostic for the cancer. The test sample can be assayed for an increased level of semenogelin in (b) by comparing the level of semenogelin in the test sample to the level of semenogelin in a control sample obtained from one or more cancer-free male mammals of the same species, wherein an increase in the level of semenogelin in the test sample as compared to the control sample is diagnostic for the cancer. Alternatively, the level of semenogelin in the test sample can be compared to an already determined range of semenogelin for cancer-free male mammals of the same species.

In addition, the invention provides a method of diagnosing cancer in a female mammal. The method comprises: (a) obtaining a test sample from the female mammal, and (b) assaying the test sample for the presence of semenogelin, wherein the presence of semenogelin in the test sample is diagnostic for the cancer.

For purposes of the invention, when a female mammal is being diagnosed, the presence of any cancer can be assayed for. A male mammal, however, can be assayed for any cancer other than prostate cancer. Preferably, the cancer is of epithelial origin, such as lung cancer, papillary renal cell carcinoma, colon cancer, and melanoma. Most preferably, the cancer is small-cell lung cancer (hereinafter referred to as "SCLC").

The test sample used in conjunction with the invention can be any of those typically used in the art. For example, the test sample can be tissue. Typically, the tissue is metastatic (e.g., cancerous) and is obtained by means of a biopsy. Such tissue can include bone marrow, lymph nodes, skin, and any organ that may develop cancerous cells. Preferably, however, the test sample is taken from a source in which secreted proteins will be most prevalent. Accordingly, the test sample is preferably serum, wherein the serum is obtained from methods known in the art, such as a blood sample.

A number of assays are contemplated for use in the present inventive methods of diagnosing cancer. A number of these assays are described in Sambrook et al., *Molecular Cloning: A Laboratory Manual*, $2^{nd}$ Ed., Cold Spring Harbor Press, Cold Spring Harbor, N.Y., 1989. Microarrays, such as those described in U.S. Pat. Nos. 6,197,506 and 6,040,138, also can be used to detect and quantify semenogelin. It will be understood that the type of assay used will depend on whether DNA, RNA or a protein (or a polypeptide thereof) is being assayed.

As used herein, the term "increased level" can be defined as detecting semenogelin in a male mammal at a level above that which is considered normal. For example, the level of semenogelin in a test sample is increased when the copy number of the gene encoding the semenogelin is greater than 1, the mRNA encoding semenogelin is about 0.001-1%, or semenogelin (or a polypeptide thereof) is detected in an amount of about 1-10,000 ng/ml.

When a nucleic acid (i.e., DNA or RNA) is assayed, various assays can be used to measure the presence and/or level of nucleic acid present. For example, when only the detection of semenogelin is necessary to diagnose effectively the cancer, such as in diagnosing a female mammal, assays including PCR and microarray analysis can be used. In certain embodiments, such as in diagnosing a male mammal, it will be necessary to detect the quantity of semenogelin present. In these embodiments, it will be advantageous to use various hybridization techniques known in the art that can effectively measure the level of semenogelin in a test sample. When the semenogelin comprises DNA, such hybridization techniques can include, for example, Southern hybridization (i.e., a Southern blot), in situ hybridization and microarray analysis. Similarly, when the semenogelin comprises RNA, Northern hybridization (i.e., a Northern blot), in situ hybridization and microarray analysis are contemplated.

It will be understood that, in such assays, a nucleic acid sequence that specifically binds to or associates with a nucleic acid encoding semenogelin, whether DNA or RNA, can be attached to a label for determining hybridization. A wide variety of appropriate labels are known in the art, including fluorescent, radioactive, and enzymatic labels as well as ligands, such as avidin/biotin, which are capable of being detected. Preferably, a fluorescent label or an enzyme tag, such as urease, alkaline phosphatase or peroxidase, is used instead of a radioactive or other environmentally undesirable label. In the case of enzyme tags, colorimetric indicator substrates are known which can be employed to provide a detection means visible to the human eye or spectrophotometrically to identify specific hybridization with complementary semenogelin nucleic acid-containing samples.

When a nucleic acid encoding the semenogelin is amplified in the context of a diagnostic application, the nucleic acid used as a template for amplification is isolated from cells contained in the test sample, according to standard methodologies. (Sambrook et al., *Molecular Cloning: A Laboratory Manual*, $2^{nd}$ Ed., Cold Spring harbor Press, Cold Spring harbor, N.Y., 1989). The nucleic acid can be genomic DNA or fractionated or whole cell RNA. Where RNA is used, it can be desirable to convert the RNA to cDNA.

In a typical amplification procedure, pairs of primers that selectively hybridize to nucleic acids corresponding to semenogelin are contacted with the nucleic acid under conditions that permit selective hybridization. Once hybridized, the nucleic acid-primer complex is contacted with one or more enzymes that facilitate template-dependent nucleic acid synthesis. Multiple rounds of amplification, also referred to as "cycles," are conducted until a sufficient amount of amplification product is produced.

Various template-dependent processes are available to amplify the semenogelin present in a given test sample. As with the various assays, a number of these processes are described in Sambrook et al. (1989), supra. One of the best-known amplification methods is the polymerase chain reaction (PCR). Similarly, a reverse transcriptase PCR (RT-PCR) can be used when it is desired to convert mRNA into cDNA. Alternative methods for reverse transcription utilize thermostable DNA polymerases and are described in WO 90/07641, for example.

Other methods for amplification include the ligase chain reaction (LCR), which is disclosed in U.S. Pat. No. 4,883, 750; isothermal amplification, in which restriction endonucleases and ligases are used to achieve the amplification of target molecules that contain nucleotide 5'-[alpha-thio]-triphosphates in one strand (Walker et al., *Proc. Natl. Acad. Sci. USA* 89: 392-396 (1992)); strand displacement amplification (SDA), which involves multiple rounds of strand displacement and synthesis, i.e., nick translation; and repair chain reaction (RCR), which involves annealing several probes throughout a region targeted for amplification, followed by a repair reaction in which only two of the four bases are present. The other two bases can be added as biotinylated derivatives for easy detection. Target-specific sequences also can be detected using a cyclic probe reaction (CPR). In CPR, a probe having 3' and 5' sequences of non-specific DNA and a middle sequence of specific RNA is hybridized to DNA, which is present in a sample. Upon hybridization, the reaction is treated with RNase H, and the products of the probe are identified as distinctive products, which are released after digestion. The original template is annealed to another cycling probe and the reaction is repeated. A number of other amplification processes are contemplated; however, the invention is not limited as to which method is used.

Following amplification of the semenogelin, it can be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al. (1989), supra.

Alternatively, chromatographic techniques can be employed to effect separation. There are many kinds of chromatography which can be used in the context of the present inventive methods e.g., adsorption, partition, ion-exchange and molecular sieve, and many specialized techniques for using them including column, paper, thin-layer and gas chromatography (Freifelder, *Physical Biochemistry Applications to Biochemistry and Molecular Biology*, $2^{nd}$ Ed., Wm. Freeman and Co., New York, N.Y. (1982)).

Amplification products must be visualized in order to confirm amplification of the semenogelin sequence. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified semenogelin sequence. The probe preferably is conjugated to a chromophore but may be radiolabeled. In another embodiment, the probe is conjugated to a binding partner, such as an antibody or biotin, where the other member of the binding pair carries a detectable moiety (i.e., a label).

One example of the foregoing is described in U.S. Pat. No. 5,279,721, which discloses an apparatus and method for the automated electrophoresis and transfer of nucleic acids. The apparatus permits electrophoresis and blotting without external manipulation of the gel and is ideally suited to carrying out methods according to the present invention.

It will be understood that the probes described above are limited in as much as any nucleic-acid sequence can be used as long as the nucleic acid sequence is hybridizable to nucleic acids encoding semenogelin or functional sequence analogs thereof. For example, a nucleic acid of partial sequence can be used to quantify the expression of a structurally related gene or the full-length genomic or cDNA clone from which it is derived.

Preferably, the hybridization is done under high stringency conditions. By "high stringency conditions" is meant that the probe specifically hybridizes to a target sequence in an amount that is detectably stronger than non-specific hybridization. High stringency conditions, then, would be conditions which would distinguish a polynucleotide with an exact complementary sequence, or one containing only a few scattered mismatches from a random sequence that happened to have a few small regions (e.g., 3-10 bases) that matched the probe. Such small regions of complementarity, are more easily melted than a full-length complement of 14-17 or more bases and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the probe and the template or target strand, and are particularly suitable for detecting expression of specific semenogelins. It is generally appreciated that conditions can be rendered more stringent by the addition of increasing amounts of formamide.

When a semenogelin protein or polypeptide fragment thereof is assayed, various assays (i.e., immunobinding assays) are contemplated to either detect or measure the quantity of semenogelin. For example, the semenogelin can comprise the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27. If desired, the semenogelin can comprise an amino acid sequence, which is specific for SgI or SgII. For example, the semenogelin assayed for can be SgI and can comprise the amino acid sequence of SEQ ID NO:2, SEQ ID NO:4, and SEQ ID NO:6. Alternatively, the semenogelin assayed for can be SgII and can comprise the amino acid sequence of SEQ ID NO:1, SEQ ID NO:3, and SEQ ID NO:5. In such embodiments, the semenogelin can be employed to detect antibodies having reactivity therewith, or, alternatively, antibodies can be prepared and employed to detect the semenogelin. The steps of various useful immunodetection assays have been described in Nakamura et al., Handbook of *Experimental Immunology* (4th Ed.), Wol. 1, Chapter 27, Blackwell Scientific Publ., Oxford (1987); Nakamura et al., *Enzyme Immunoassays: Heterogenous and Homogenous Systems*, Chapter 27 (1987) and include Western hybridization (i.e., Western blots), immunoaffinity purification, immunoaffinity detection, enzyme-linked immunosorbent assay (e.g., an ELISA), and radioimmunoassay. A microarray also can be used to detect or measure the levels of semenogelin.

In general, the immunobinding assays involve obtaining a test sample suspected of containing a protein, peptide or antibody corresponding to a semenogelin, and contacting the sample with an antibody in accordance with the present invention, as the case may be, under conditions effective to allow the formation of immunocomplexes. Indeed, a mammal can be diagnosed with a cancer by either detecting SgI, SgII, or an antibody that recognizes semenogelin, such as when a female mammal is being tested, or by quantifying the levels of SgI, SgII, or an antibody that recognizes semenogelin, such as when a male mammal is being tested.

Any suitable antibody can be used in conjunction with the present invention such that the antibody is specific for semenogelin, and in particular, SgI and/or SgII. One known antibody which has such specificity is MHS-5. Indeed, MES-5 is a monoclonal antibody that can recognize both SgI and SgII, as well as several proteolytic fragments thereof. Additionally, the antibody can recognize other antibodies present in a test sample that bind to semenogelin. Indeed, when such an anti-idiotypic antibody is used, it will typically recognize MHS-5.

The immunobinding assays for use in the present invention include methods for detecting or quantifying the amount of semenogelin in a sample, which methods require the detection or quantitation of any immune complexes formed during the binding process. Here, a test sample suspected of containing a semenogelin would be obtained from a mammal and subsequently contacted with an antibody (e.g., MHS-5). The detection or the quantification of the amount of immune complexes formed under the specific conditions is then performed.

Contacting the biological sample with an antibody that recognizes a semenogelin under conditions effective and for a period of time sufficient to allow formation of immune complexes (primary immune complexes) is generally a matter of simply adding the antibody to the sample and incubating the mixture for a period of time long enough for the antibodies to form immune complexes with, i.e., to bind to, any antigens. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well-known in the art and can be achieved through the application of numerous approaches. These methods are generally based upon the detection of a label or marker, such as any radioactive, fluorescent, biological or enzymatic tags or labels of standard use in the art. U.S. Patents concerning the use of such labels include U.S. Pat. Nos. 3,817,837, 3,850,752, 3,939,350, 3,996,345, 4,277,437, 4,275,149 and 4,366,241. Of course, additional advantages can be realized by using a secondary binding ligand, such as a second antibody or a biotin/avidin ligand binding arrangement, as is known in the art.

The antibody which is used in the context of the present invention can, itself, be linked to a detectable label, wherein one would then simply detect this label, thereby allowing the presence of or the amount of the primary immune complexes to be determined.

Alternatively, the first added component that becomes bound within the primary immune complexes can be detected by means of a second binding ligand that has binding affinity for the first antibody. In these cases, the second binding ligand is, itself, often an antibody, which can be termed a "secondary" antibody. The primary immune complexes are contacted with the labeled, secondary binding ligand, or antibody, under conditions effective and for a period of time sufficient to allow the formation of secondary immune complexes. The secondary immune complexes are then washed to remove any non-specifically bound labeled secondary antibodies or ligands, and the remaining label in the secondary immune complexes is then detected.

Further methods include the detection of primary immune complexes by a two-step approach. A second binding ligand, such as an antibody, that has binding affinity for the first antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed.

It will be understood that other diagnostic tests can be used in conjunction with the diagnostic tests described herein to enhance further the accuracy of diagnosing a mammal with a cancer. For example, a monoclonal antibody, such as the ones described in U.S. Pat. No. 4,569,788 can be used effectively in diagnosing small-cell lung cancer over non small-cell lung cancer.

The present invention also provides a method of prognosticating a cancer in a mammal, wherein the cancer is other than prostate cancer and semenogelin is a marker for the cancer, which method comprises measuring the level of semenogelin in a test sample obtained from the mammal, wherein the level of semenogelin in the test sample is indicative of the prognosis of the cancer in a mammal. The level of semenogelin in the test sample can be measured by comparing the level of semenogelin in another test sample obtained from the mammal over time in accordance with the methods described above. An increase in semenogelin from one sample to the next is indicative of growth and/or metastasis of the cancer, whereas a decrease in semenogelin from one sample to the next is indicative of reduction of the cancer.

The invention also provides a method of assessing the effectiveness of treatment of a cancer in a mammal, wherein the cancer is other than prostate cancer and semenogelin is a marker for the cancer, which method comprises measuring the level of semenogelin in a test sample obtained from the mammal, wherein the level of semenogelin in the test sample is indicative of the effectiveness of the treatment of the cancer in the mammal. The level of semenogelin in the test sample can be measured by comparing the level of semenogelin in the test sample to the level of semenogelin in another test sample obtained from the mammal over time in accordance with the methods described above. An increase in semenogelin from one sample to the next is indicative of the treatment being ineffective, whereas no change or a decrease in semenogelin from one sample to the next is indicative of the treatment being effective.

Although semenogelin is known to be a secreted protein, semenogelins are expressed ectopically by cancer cell lines, in particular SCLC cell lines derived from both male and female mammals. Furthermore, membrane association of semenogelin proteins is enhanced by the addition of epidermal growth factor (EGF) when the cells are attached to thrombospondin-1 peptides. Thrombospondin-1 is a peptide known to bind to integrins on a tumor cell surface. Integrins are cell-surface receptors responsible for the attachment of cells to the extracellular matrix. As a result, semenogelin associates with a thrombospondin-1 peptide, which, in turn, associates with an integrin on the surface of the tumor cell. This process is enhanced with the addition of EGF. Accordingly, the present invention further provides a method of inducing an immune response to a cancer in a mammal, wherein the cancer is other than prostate cancer and semenogelin is a marker for the cancer. The method comprises administering to the mammal a composition comprising (a) an immune-response inducing effective amount of (i) a semenogelin protein or polypeptide fragment thereof, or (ii) an antibody or antigenically reactive fragment thereof that is specific for a semenogelin protein or polypeptide fragment thereof, or (b) a recombinant vector encoding and expressing an immune-response inducing effective amount of (i) or (ii), whereupon an immune response to the cancer is induced. For example, the method of inducing an immune response to the mammal can comprise administering to the mammal a composition comprising (a) an immnune-response inducing effective amount of (i) a polypeptide of SEQ D NO:1, SEQ ID NO:2, SEQ ID NO:3, SEQ D NO:4, SEQ ID NO:5, SEQ D NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 or (ii) an antibody or antigenically reactive fragment thereof that is specific for a polypeptide of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 or (b) a recombinant vector encoding and expressing an immune-response inducing effective amount of (i) or (ii), whereupon an immune response to the cancer is induced.

The present invention also provides a composition. The composition comprises a pharmaceutically acceptable carrier and (a) an immune-response inducing effective amount of (i) a polypeptide of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:1, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 or (ii) an antibody or antigenically reactive fragment thereof that is specific for a polypeptide of SEQ ID NO:1, SEQ ID NO:2, SEQ BD NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:1, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 or (b) a recombinant vector encoding and expressing an immune-response inducing effective amount of (i) or (ii).

The semenogelin protein or polypeptide fragment thereof of (i) and the antibody or antigenically reactive fragment thereof of (ii) can be purified and isolated from a naturally occurring source or can be synthetically produced. Alternatively, the semenogelin protein or polypeptide fragment thereof of (i) and the antibody or antigenically reactive fragment thereof of (ii) can be recombinantly produced. In this respect, the recombinant vector of (b) comprises a nucleic acid sequence which encodes and expresses an immune-response inducing effective amount of (i) or (ii). Methods of recombinant production and synthesis are known in the art (see, e.g., Sambrook et al. (1989), supra) as are methods of antibody production (see, e.g., Antibodies: A Laboratory Manual, Cold Spring Harbor Laboratory, (1988)). In accordance with the present invention, an antigenically reactive fragment of the antibody (e.g., Fab, Fc, etc.) can be obtained from the antibodies produced as described above, by methods which include digestion with enzymes, such as pepsin or papain, and/or cleavage of disulfide bonds by chemical reduction.

If the semenogelin protein or polypeptide fragment of (i) and the antibody or antigenically reactive fragment thereof of (ii) are recombinantly produced, any suitable recombinant vector can be used. Suitable vectors include, for example, plasmid vectors, retroviral vectors, adenoviral vectors, adeno-associated viral vectors, vaccinia virus, sindbis virus, cytomegalovirus, herpes simplex virus, defective hepatitis B viruses, and any other vector or vector system known in the art.

The composition can comprise more than one active ingredient, such as more than one semenogelin of the present invention. Alternatively, or additionally, the composition can comprise another pharmaceutically active agent or drug.

The carrier can be any suitable carrier. Preferably, the carrier is a pharmaceutically acceptable carrier. With respect to compositions, the carrier can be any of those conventionally used and is limited only by chemico-physical considerations, such as solubility and lack of reactivity with semenogelin, and by the route of administration. It will be appreciated by one of skill in the art that, in addition to the above-described composition, the compositions of the present inventive methods can be formulated as inclusion complexes, such as cyclodextrin inclusion complexes, or liposomes.

The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the semenogelin and one which has no detrimental side effects or toxicity under the conditions of use.

The choice of carrier will be determined in part by the particular semenogelin, as well as by the particular method used to administer the composition. Accordingly, there are a variety of suitable formulations of the composition of the present invention. The following formulations for oral, aerosol, parenteral, subcutaneous, intravenous, intramuscular, interperitoneal, rectal, and vaginal administration are exemplary and are in no way limiting.

The method of inducing an immune response to a cancer using a composition of the present invention can be made more effective by administering one or more other anticancer compounds along with one or more other compositions of the present invention. These other anticancer compounds include, but are not limited to, all of the known anticancer compounds approved for marketing in the United States and those that will become approved in the future. See, for example, Table 1 and Table 2 of Boyd, *Current Therapy in Oncology*, Section I. Introduction to Cancer Therapy (J. E. Niederhuber, ed.), Chapter 2, by B. C. Decker, Inc., Philadelphia, 1993, pp. 11-22. More particularly, these other anticancer compounds include doxorubicin, bleomycin, vincristine, vinblastine, VP-16, VW-26, cisplatin, carboplatin, procarbazine, and taxol for solid tumors in general; alkylating agents, such as BCNU, CCNU, methyl-CCNU and DTIC, for brain or kidney cancers; and antimetabolites such as 5-FU and methotrexate for colon cancer.

One skilled in the art will appreciate that suitable methods of administering a composition of the invention to a mammal, in particular a human, are available, and, although more than one route can be used to administer a particular compound, a particular route can provide a more immediate and more effective reaction than another route. Accordingly, the herein-described methods are exemplary and are in no way limiting.

The dose administered to a mammal, in particular a human, should be sufficient to induce an immune response to the cancer. One skilled in the art will recognize that dosage will depend upon a variety of factors including the strength of the particular composition employed, as well as the age, species, condition, and body weight of the mammal. The size of the dose will also be determined by the route, timing, and frequency of administration as well as the existence, nature, and extent of any adverse side-effects that might accompany the administration of a particular composition and the desired physiological effect.

Suitable doses and dosage regimens can be determined by conventional range-finding techniques known to those of ordinary skill in the art. Generally, a composition is initially administered in smaller dosages, which are less than the optimum dose of the composition. Thereafter, the dosage is increased by small increments until the optimum effect under the circumstances is reached. The present inventive method will typically involve the administration of about 0.1-100 mg of one or more of the compositions described above per kg body weight.

EXAMPLES

The following examples further illustrate the invention but, of course, should not be construed as in any way limiting its scope.

A number of assays are used in the examples below, including isoelectric focusing, 2-dimensional gel electrophoresis, SDS-polyacrylamide gel electrophoresis, Western blotting, mass spectrometry, and liquid chromatography. The first four are described in Alberts et al., *Molecular Biology of the Cell*, $3^{rd}$ Ed., Garland Publishing, Inc., New York, N.Y. (1994), mass spectrometry is described in Skoog et al., *Principles of Instrumental Analysis*, Holt, Rinehart and Winston, Inc. (1971), and liquid chromatography is described in Mohrig-Neckers, *Laboratory Experiments in Organic Chemistry*, $2^{nd}$ Ed. Litton Educational Publishing, Inc., New York, N.Y. (1973).

Example 1

This example demonstrates that semenogelin is expressed ectopically by SCLC and melanoma cell lines.

A synthetic peptide containing the thrombospondin-1 sequence, FQGVLQNVRFVF (peptide 678; SEQ ID NO:28), that binds to the α$\beta$1 integrin was prepared as described in Krutzsch et al., *J. Biol. Chem.*: 24080-24086 (1999). Semenogelin was purified from seminal plasma as described in Malm, *Eur. J. Biochem.* 238: 48-53 (1996), and recombinant EGF was obtained from R & D Systems (Minneapolis, Minn.) for use in the following assays.

Two different types of cancer cell lines were tested for semenogelin. Specifically, lung cancer (OH-1, NCI-N592, NCI-N417, NCI-H378, NCI-H570, NCI-H727, NCI-H157, NCI-H520, NCI-A549) and melanoma (C32, A2058) cell lines were grown in RPMI 1640 medium containing 10% fetal calf serum (15% FCS for OH-1 cells) until log phase.

The lung cancer and melanoma cell lines' were then dissociated by replacing the growth medium with 2.5 mM EDTA in phosphate-buffered saline and incubating at 37° C. for 10 minutes. Cells were then triturated and collected by centrifugation, suspended in M199 medium, and plated on thrombospondin-1 peptide coated plates (Falcon 1029). Cell adhesion to thrombospondin-1 peptide 678 (10 p was assessed with and without EGF (5 ng/ml). Cells were incubated for 2 hours at 37° C. and then aspirated and washed three times with Dulbecco's PBS. Cytoskeleton-associated adhesion complexes were isolated by detergent extraction of the cells using CSK buffer (0.5% Triton-X-100, 50 mM NaCl, 300 mM sucrose, 3 mM MgCl2, 20 μg/ml aprotinin, 1 μg/ml leupeptin, 1 μg/ml pepstatin, 1 mM phenylmethanesulfonyl fluoride, 10 mM piperazine-N,N'-bis-(2-ethanesulfonic acid), pH 6.8) for 1 minute followed by sonication for 30 seconds to remove cell bodies. The cell-surface adhesion complexes, which remained attached to the peptide substrates, were then extracted using 0.5 mL of IX RIPA buffer (50 mM Tris pH 7.2, 1% Triton-X-100, 1% deoxycholate, 0.1% SDS, 150 mM NaCl, 1 mM phenylmethanesulfonyl fluoride). The plates were scraped, the recovered extracts were centrifuged, and the supernatant fractions were collected.

Proteins extracted from the thrombospondin-1 peptide-associated adhesion complexes were mixed with an equal volume of rehydration buffer (8 M urea, 1% IPG, 2% CHAPS in $H_2O$) in a strip holder with a gel strip, pH 3-10 (Amersham Pharmacia Biotech, Piscataway, N.J.) and incubated overnight at 20° C. The strip holders and hydrated strips were placed in an IPGphor unit and subjected to isoelectric focusing for 4 hours. The gels were then equilibrated with 100 mg dithiothreitol in 10 ml $H_2O$ for 1 hour, followed by the addition of 100 mg of iodoacetamide and shaking for 15 minutes. The equilibrated gel strip was applied to a sodium dodecyl sulfate/10% polyacrylamide gel and subjected to electrophoresis (i.e., 2-D gel electrophoresis) on a Hoefer TE Transphor for 15 minutes at 20 mA, then 5 hours at 40 mA. The gels were removed and stained with Coomassie blue stain for 1 hour and destained (10% acetic acid +35% methanol in $H_2O$) overnight.

Analysis of adhesion complexes isolated from both lung cancer and melanoma cells by 2-dimensional gel electrophoresis showed that two proteins with molecular weights of 25-58 kDa and a pI of 9 were induced to associate with the adhesion complexes by the addition of EGF. The two protein spots were isolated and sequenced by mass spectrometry and found to contain multiple peptides homologous to portions of SgI and SgII.

As indicated by these results, semenogelin is expressed ectopically by SCLC and melanoma cell lines. Moreover, the membrane association of the semenogelin proteins to a cancer cell was enhanced by the addition of EGF when the cancer cell(s) was attached to thrombospondin-1 peptides via an α$\beta$B1 integrin.

Example 2

This example also demonstrates that semenogelin is expressed in lung cancer and melanoma cell lines.

Lung cancer and melanoma cell lines were harvested and extracted as described above. Extracted proteins, after clarifying by centrifugation, were separated by SDS-polyacrylamide gel electrophoresis in Mini Protean II System (BioRad-Hercules, Calif.) for 55 minutes at 170V. Following electrophoresis, proteins were transferred onto polyvinylidine difluoride membrane in transfer buffer (20% methanol in 1×Tris/glycine, BioRad) at 70V for 2.5 hours and washed three times with 1×Tris/glycine buffer. The membrane was blocked overnight in Dulbecco's PBS containing 1% bovine serum albumin and 0.1% Tween-20. The blot was then incubated with biotinylated MHS-5 antibody (Humagen Fertility Biagnostics, Charlottesville, Va.) at 1:1000 for 2 hours at 37° C. followed by four washes with Dulbecco's PBS containing 0.1% Tween. The membrane was then incubated with strepta-vidin-horseradish peroxidase (Amersham Pharmacia Biotech) diluted 1:20,000 for 1 hour. Surface proteins were visualized with an chemiluminescent detection kit (Amersham Pharmacia Biotech).

Additionally, unlabeled MHS-5 antibody was pre-bound to Protein A agarose in Dulbecco's PBS containing 1% BSA and 0.1% Tween-20 for 2 hours at 4° C. Beads containing the bound antibody were then incubated with 500 μL of extracted proteins overnight at 4° C. The beads were washed three times with Tris-buffered saline, then eluted by heating with sample buffer (50 mM Tris, 6 M urea, 30% glycerol, 2% SDS, and bromophenol blue) at 95° C. for 5 minutes, and separated and transferred as described previously. The blot was then incubated with biotinylated MHS-5 antibody, streptavidin-horseradish peroxidase, and visualized by chemiluminescence.

Proteins of interest contained in 1- or 2-dimensional gels were analyzed by liquid chromatography/mass spectrometry (LC/MS) to determine their identity. The protein spot detected in the stained gel was excised and placed in a microfuge tube. The gel piece was washed with methanol/ammonium bicarbonate buffer, dried in vacuo, then treated with trypsin overnight. The resulting peptides were extracted, separated, and analyzed on a Finnigan LCQ LC/MS system. The resulting run files were first analyzed using Sequest database searching software. If no identification resulted, then further database searching and/or de novo sequencing was carried out.

Mass spectrometric analyses of tryptic peptides from these two fragments yielded peptides that covered 42.6% of the SgI protein sequence and 38.5% of the SgII protein sequence. Several peptides detected were identical in both proteins, as expected from their known sequence homologies. These peptides are described in Table 1. However, several of the ion peaks were assigned to peptides that could be assigned specifically to semenogelin I or II. These resulting polypeptides are described in Table 2.

TABLE 1

| SEQ ID NO: | Peptide Sequence | Position in Complete Amino Acid Sequence |
| --- | --- | --- |
| 7 | ISYQSSSTEER | 406-416 |
| 8 | IPSQAQEYGHK | 392-402 |
| 9 | GQHYFGQK | 45-52 |
| 10 | SQNQVTIPSQDQEHGHK | 446-462 |
| 11 | KSQQYDLNALHK | 81-92 |
| 12 | SQIQTPNPNQDQWSGQNAK | 506-524 |
| 13 | GSISIQTEEKIHGK | 432-445 |
| 14 | SQQYDLNALHK | 82-92 |
| 15 | GHFHMIVIHHK | 121-131 |
| 16 | LWVHGLSK | 166-173 |
| 17 | DVSQSSISFQIEK | 488-500 |
| 18 | GSFSIQHTYHVDINDHDWTR | 61-80 |
| 19 | TQGGSQSSYVLQTEELVVNK | 186-205 |
| 20 | HLAQHLNNDR | 448-457 |
| 21 | GISSQYSNTEER | 154-165 |
| 22 | LHYGENGVQK | 358-367 |
| 23 | DVSQSSIYSQTEEK | 308-321 |
| 24 | QITIPSQEQEHSQK | 329-342 |
| 25 | LPSEFSQFPHGQK | 32-44 |
| 26 | HQHGSHGGLDIVIIEQEDDSDR | 426-447 |
| 27 | DIFSTQDELLVYNK | 252-265 |

TABLE 2

| SEQ ID NO: | Peptide Sequence | Semenogelin | Position in Complete Amino Acid Sequence |
| --- | --- | --- | --- |
| 1 | QHLGGSQQLLNYK | SgII | 98-110 |
| 2 | HLGGSQQLLHNK | SgI | 98-110 |
| 3 | GHYQNVVDVR | SgII | 218-227 |
| 4 | GHYQNVVEVR | SgI | 218-227 |
| 5 | QDLLSHEQK | SgII | 535-543 |
| 6 | EQDLLSHEQK | SgI | 414-423 |

Nearly all SCLC lines screened by Western blotting demonstrated the presence of a doublet between 70-80 kDa corresponding to SgII. Only the classic SCLC cell line in OH-1, which grows as tight aggregates in vitro, was positive for SgI. SgII was detected in all of the SCLC and some non-SCLC lung cancer cell lines, including some squamous cell carcinomas. SgII expression was also detected in two melanoma cell lines (A2058 and C32 cell lines).

Furthermore, SgII was found in cell lines derived from SCLC patients of either gender. Expression of SgII in the female lines H378 and N417 further supports specific ectopic production of the semenogelins by the SCLC cells.

SgII was also secreted into the medium by OH-1 SCLC cells. Measurement of secreted SgII with MHS-5, therefore, can provide a quantitative method to assess SCLC tumor burden.

These results suggest that both semenogelins were cleaved somewhere in the middle of the protein to generate the observed fragments set forth in Tables 1 and 2 and evidence that semenogelin is expressed in both lung cancer and melanoma cell lines.

Example 3

This example demonstrates that semenogelin can be detected in tumor tissue samples taken from patients diagnosed with SCLC.

Formalin-fixed paraffin-embedded representative tissue specimens were taken from 13 specimens and immunostained with monoclonal antibody against MHS-5 (dilution 1/100). Staining was performed with the EnVision system (DAKO). Endogenous peroxidase activity was quenched by treatment with 5% hydrogen peroxide in methanol for 30 minutes at room temperature. Antigen retrieval using Target Retrieval pH 7.0 (DAKO) and microwave treatment for 20 minutes in an 800-watt microwave open was performed. A blocking step with protein block serum free (DAKO) was used. The primary antibody was then applied for 120 minutes at room temperature. The sections were rinsed with washing buffer (Dulbeccos PBS+0.1% Tween) at room temperature and incubated with EnVision system reagents for 30 minutes at room temperature. The slides were rinsed with washing buffer, and treated with a solution containing 0.05% diaminobenzidine hydrochloride and 0.1% hydrogen peroxide in 0.05 mol/l TRIS-buffered saline, pH 7.4, at room temperature for 5 minutes. After rinsing in distilled water for 3 minutes, the slides were counterstained with modified Harris hematoxylin, dehydrated, and mounted. Negative control sections were treated in an identical fashion except for lack of primary antibody. An appropriate positive control (human seminal vesicle) was run concurrently. Of the 13 SCLC specimens analyzed, 12 were found to be diffusely positive with homogenous, widespread antibody labeling throughout the cytoplasm of the tumor cells and surrounding matrix. These results indicate that semenogelin is ectopically expressed in SCLC cells taken directly from an individual and, thus, further evidence that semenogelin is an effective marker in diagnosing SCLC.

All of the references cited herein, including patents, patent applications, and publications, are hereby incorporated in their entireties by reference.

While this invention has been described with an emphasis upon preferred embodiments, variations of the preferred embodiments can be used, and it is intended that the invention can be practiced otherwise than as specifically described herein. Accordingly, this invention includes all modifications encompassed within the spirit and scope of the invention as defined by the claims.

What is claimed is:

1. A method of detecting semenogelin-positive lung cancer in a human male, which method comprises:
   (a) obtaining a test sample from the human male, and
   (b) assaying the test sample for an increased level of semenogelin polypeptide by comparing the level of semenogelin polypeptide in the test sample to the level of semenogelin polypeptide in a control sample obtained from one or more cancer-free human males, wherein the increased level of semenogelin polypeptide in the test sample is a diagnostic marker for lung cancer.

2. The method of claim 1, wherein the semenogelin polypeptide comprises the amino acid sequence of SEQ ID NO:1, SEQ ID NO:2, SEQ ID NO:3, SEQ ID NO:4, SEQ ID NO:5, SEQ ID NO:6, SEQ ED NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27.

3. The method of claim 1, wherein the semenogelin polypeptide is semenogelin I.

4. The method of claim 3, wherein the semenogelin I comprises the amino acid sequence of SEQ ID NO:2, SEQ ID NO:4 or SEQ ID NO:6.

5. The method of claim 1, wherein the semenogelin polypeptide is semenogelin II.

6. The method of claim 5, wherein the semenogelin II comprises the amino acid sequence of SEQ ID NO:1, SEQ ID NO:3 or SEQ ID NO:5.

7. The method of claim 1, wherein the test sample is serum or tissue.

8. The method of claim 7, wherein the tissue is tumor tissue.

9. The method of claim 1, wherein the method further comprises (c) testing for the presence of small-cell lung cancer.

10. The method of claim 1, wherein the cancer is squamous cell carcinoma.

11. The method of claim 1, wherein the lung cancer is small-cell lung cancer.

12. A composition comprising a pharmaceutically acceptable carrier and an immune-response inducing effective amount of a polypeptide fragment of semenogelin, said polypeptide fragment consisting of the polypeptide of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27.

13. The method of claim 1, wherein the test sample is serum.

14. The method of claim 13, wherein the serum comprises small-cell lung cancer cells.

15. The method of claim 10, wherein the test sample comprises cells or extracellular matrix from the lung.

16. The method of claim 11, wherein the test sample comprises cells or extracellular matrix from the lung.

* * * * *

UNITED STATES PATENT AND TRADEMARK OFFICE
CERTIFICATE OF CORRECTION

PATENT NO.      : 7,618,789 B2                         Page 1 of 1
APPLICATION NO. : 10/474213
DATED           : November 17, 2009
INVENTOR(S)     : Roberts et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1148 days.

Signed and Sealed this

Twenty-sixth Day of October, 2010

David J. Kappos
*Director of the United States Patent and Trademark Office*